(12) United States Patent
Shan et al.

(10) Patent No.: US 6,566,089 B1
(45) Date of Patent: *May 20, 2003

(54) CELL-BASED DRUG SCREENS FOR REGULATORS OF GENE EXPRESSION

(75) Inventors: Bei Shan, South San Francisco, CA (US); R. Marc Learned, South San Francisco, CA (US); M. Catherine Amaral, South San Francisco, CA (US); Steven L. McKnight, South San Francisco, CA (US); Fabienne Charles de la Brousse, South San Francisco, CA (US); Jin-Long Chen, South San Francisco, CA (US)

(73) Assignee: Tularik Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/866,942

(22) Filed: May 31, 1997

Related U.S. Application Data (63) Continuation-in-part of application No. 08/707,408, filed on Sep. 4, 1996, now Pat. No. 5,780,258.

(51) Int. Cl.$^7$ .................................................. C12Q 1/32
(52) U.S. Cl. ........................ 435/29; 435/69.1; 424/9.1
(58) Field of Search .................. 435/6, 69.1, 320.1, 435/29; 424/9.1; 800/2

(56) References Cited

U.S. PATENT DOCUMENTS 5,665,543 A  *  9/1997  Foulkes et al. ................. 435/6
5,720,936 A  *  2/1998  Wadsworth et al. .......... 424/9.1

FOREIGN PATENT DOCUMENTS

WO    91/06667    *   5/1991

* cited by examiner

*Primary Examiner*—Remy Yucel
(74) *Attorney, Agent, or Firm*—Richard Aron Osman (57) ABSTRACT

The invention provides methods and compositions for screening for pharmacological agents which regulate gene expression in mammals. An exemplary assay involves (a) contacting a mammalian cell comprising a knock-in mutant of a targeted native allele encoding a reporter of gene expression, wherein the expression of the reporter is under the control of the gene expression regulatory sequences of the native allele, with a candidate agent under conditions whereby but for the presence of the agent, the reporter is expressed at a first expression level; and, (b) measuring the expression of the reporter to obtain a second expression level, wherein a difference between the first and second expression levels indicates that the candidate agent modulates gene expression.

13 Claims, 3 Drawing Sheets

CELL-BASED DRUG SCREENS FOR REGULATORS OF GENE EXPRESSION

CROSS REFERENCE TO RELATED APPLICATION

This application is a continuation-in-part of application Ser. No. 08/707,408 filed Sep. 4, 1996 now U.S. Pat. No. 5,780,258.

INTRODUCTION

1. Field of the Invention

The field of this invention is knock-in cell-based drug screens for regulators of targeted gene expression.

2. Background

Transcriptional regulation provides an ideal target for therapeutic intervention. A number of techniques are available for screening for drugs active at the level of gene transcription. Including in vitro assays such as binding assays (e.g. U.S. Pat. No. 5,563,036) and RNA polymerase assays (e.g. U.S. Pat. No. 5,635,349), cell-based assays such as cotransfection assays and Northern-blot analyses.

Inherent drawbacks of these in vitro and transfection-based assays include their limited recreation or modeling of the natural transcriptional process. On the other hand, Northern-blot analyses of natural transcripts are time and resource demanding and less amendable to high-throughput drug development programs.

SUMMARY OF THE INVENTION

The invention provides methods and compositions for screening for agents which regulate the level of targeted gene expression in a natural context. Such agents find use in modulating a wide variety of physiological manifestations of gene expression.

The subject assays are cell-based and generally involve contacting a mammalian cell comprising a mutant of a native allele encoding a reporter of the targeted gene expression, wherein the expression of the reporter is under the control of the native gene expression regulatory sequences of the native targeted allele, with a candidate agent under conditions whereby but for the presence of the agent, the reporter is expressed at a first expression level; and, measuring the expression of the reporter to obtain a second expression level, wherein a difference between the first and second expression levels indicates that the candidate agent modulates the expression of the targeted gene.

The mutant generally results from replacement of a portion of the native allele with a sequence encoding the reporter. For example, the cell may be a progeny of, a clone or, or genetically identical to a genetic knock-in cell made by homologous recombination of the native allele with a transgene comprising a sequence encoding the reporter flanked by flanking sequences capable of effecting the homologous recombination of the transgene with the native allele, a positive selectable marker positioned inside the flanking sequences and optionally, a negative selectable marker positioned outside the flanking sequences. The cell may be a primary cell residing in or isolated from an animal transgenic in the mutant or derive from a cultured cell line transgenic in the mutant.

The invention also encompasses mammalian cells and mammals transgenic in a mutant of a native allele encoding a reporter of gene expression, wherein the expression of the reporter is under the control of the gene expression regulatory sequences of the native allele, genetic knock in vectors for making such animals and cells and methods of making and using such vectors, cells and animals.

DETAILED DESCRIPTION OF THE INVENTION

The general assays involve contacting a cell having a reporter for targeted gene expression with a candidate agent and monitoring reporter expression to determine if the agent has a specific effect on targeted gene expression. To accurately reflect targeted gene expression, the reporter gene is positioned within the targeted gene, resident at its native locus in the genome, such that effects of the mutation on transcription and translation at the locus, as compared with the corresponding wild-type allele, are minimized. Generally, all the native gene sequences 5' and 3' to the native transcriptional start and stop sites are retained in the mutant allele, as are preferably all the native sequences 5' and 3' to the native translational start and termination sites, where the targeted gene has translational stop and strart sites. Hence, the transcriptional and any translational start and termination sites of the native gene are preferably retained and used for the reporter. The reporter may be encoded at the translational start site or in frame within the structural gene. Hence, the reporter may be expressed free or as a fusion product with N- and/or C-terminal sequences of the targeted gene encoded polypeptide, e.g. the reporter gene may be an insertion or partial replacement of coding sequence.

Preferred reporter genes are readily expressed by the host cells and provide products that are readily detected and quantified. Exemplary reporter genes include β-galactosidase, CAT, GFP and, preferably, luciferase. The mutated locus may also comprise a positive selection marker such as an antibiotic resistance gene, e.g. neomycin, residual from the initial construction of the mutation. Alternatively, such residual sequences may be lost or removed, e.g. using a Loxp-CRE recombination system, in the course of cell passage or animal reproduction.

The assayed cells are clones of, genetically identical to, or, preferably progeny of a genetic knock-in cell made by homologous recombination, e.g. recombination of the native targeted allele with a transgene comprising a sequence encoding the reporter flanked by flanking sequences capable of effecting the homologous recombination of the transgene with the native allele, a positive selectable marker positioned inside the flanking sequences and, optionally, a negative selectable marker positioned outside the flanking sequences (see Experimental Section, below). The cells used in the assays are preferably differentiated which refers to cells which demonstrate at least some cell-type specific gene expression. Such cells are identified by any of cell-type specific gene expression (e.g. ob gene expression), cell-type specific markers, or cell-type specific morphology. A wide variety of cell types are amenable to the methods. Exemplary cell types include fluid (e.g. blood) borne cell types such as lymphocytes, macrophages, etc., and preferably, structurally associated cells types such as adipocytes, hepatocytes, muscle cells, neurons, etc. The cells may be mature cell types or precursor cells, such as preadipocytes, cultured ES cells (see, e.g. Pedersen (1994) Reprod. Fertil. Dev., 6, 543–552), etc. The cells may be primary cells isolated from an animal transgenic in the mutant or derive from a cultured cell line transgenic in the mutant. Primary cells are preferably rodent, more preferably mouse or rat cells and are preferably dissociated and substantially isolated from other cell types prior to use. Cell lines may be made by gene targeting into established cell lines such as 3T3-based cells (e.g. -L1 and -F442A), derived from the transgenic animal disclosed herein and immortalized, etc.

The targeted gene generally encodes transcript which effects, directly or through a translation product, a cellular function. A wide variety of genes may be targeted. Exemplary genes suitable for targeting include genes encoding cell signaling proteins such as leptin, receptor such as LDLR, growth factors such as TNFα, transcription factors such as STAT6, mitochondrial proteins such as UCP-2, enzymes such as CDKs, etc., and nontranslated genes such as epsilon.

An exemplary assay involves (a) contacting a mammalian cell (ex vivo for high throughput applications) comprising a mutant of a native (i.e. otherwise naturally present in the host cell or animal) allele encoding a reporter of gene expression, wherein the expression of the reporter is under the control of the native gene expression regulatory sequences (preferably both transcription regulatory elements) of the native allele, with a candidate agent under conditions whereby but for the presence of the agent, the reporter is expressed at a first expression level; and, (b) measuring the expression of the reporter to obtain a second expression level, wherein a difference between the first and second expression levels indicates that the candidate agent modulates gene expression.

EXAMPLES

Figure 3:
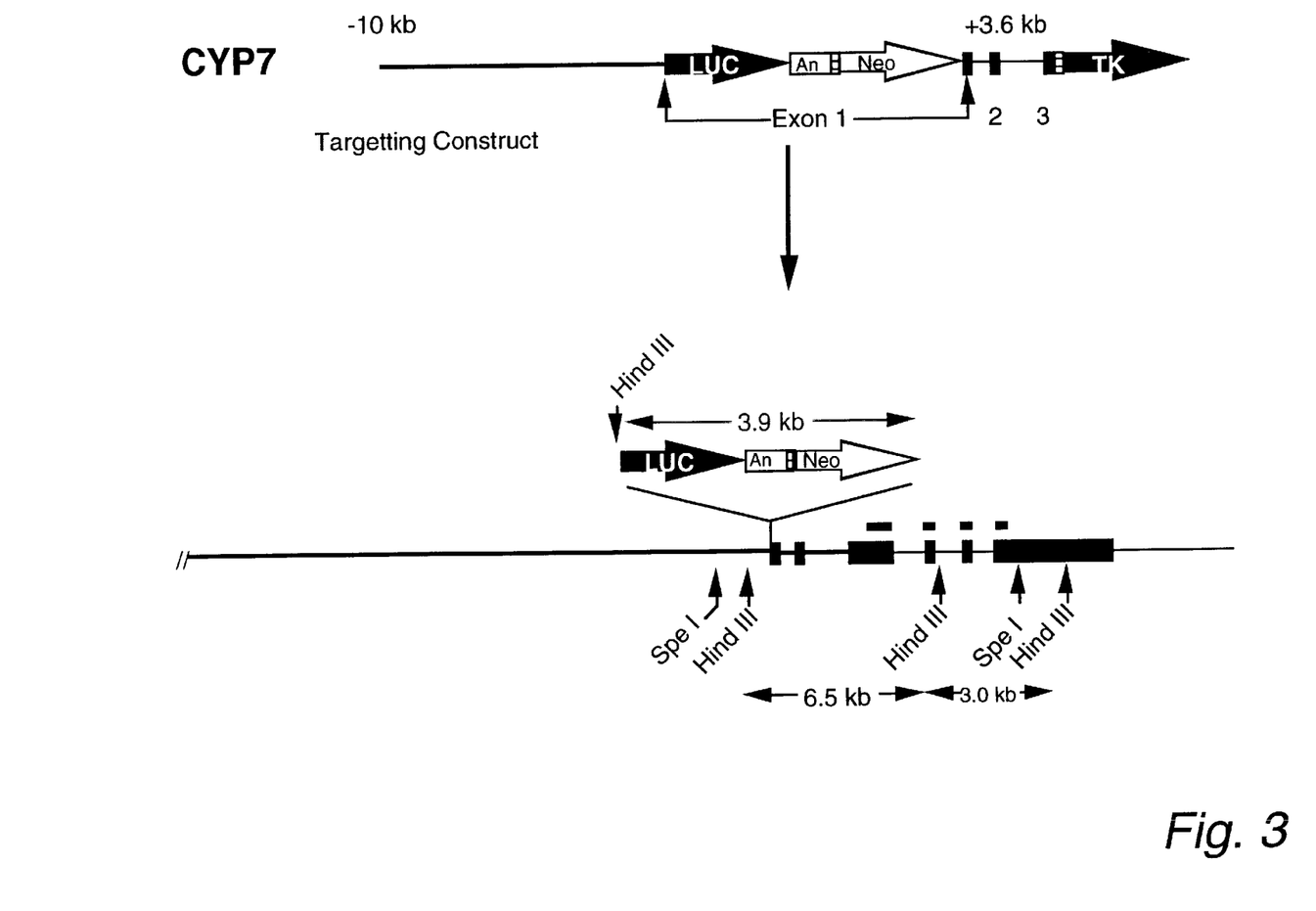
FIG. 3 shows the structure of a human CYP7-luciferase knock-in construct and the CYP7 gene structure showing the vecter insertion site.

1. Targeted Gene Replacement of Human Cholesterol 7-α Hydroxylase a. Isolation of the Human CYP7 Genomic Clone A genomic library was constructed in the λGEM11 vector using HepG2 DNA that had been partially digested with Sau3A restriction endonuclease. Recombinant phage containing the CYP7 gene were identified by hybridization to a radiolabeled CYP7 cDNA probe. From these clones, a 14 kilobasepair fragment containing sequences from approximately −10 kb to +3.6 kb (relative to transcriptional initiation) was isolated for additional characterization and modification. See FIG. 3.

b. Preparation of the CYP7:luciferase Targeting Construct

The 14 kb fragment of the CYP7 gene was modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette was inserted at position +57 in exon 1 of the CYP7 gene, positioning the reporter gene under the transcriptional control of the CYP7 promoter. The chimeric CYP7:luciferase:neo gene was subsequently cloned into the pBluescript-MC1-HSVTk plasmid to allow dual selection with G418 and gancyclovir (see FIG. 3).

c. Isolation of CYP7 "Knock-in" Cell Lines: Transfection and Selection of Stably-transformed Cell Lines The CYP7 targeting construct was introduced into HepG2 cells by electroporation. Following recovery, the cells were maintained in media supplemented 1 mg/ml G418 and 2 μM gancyclovir for 3–4 weeks until isolated colonies were observed. These G418$^R$-Ganc$^R$ cells were isolated and propagated as individual cultures for further characterization.

d. Identification of Gene Targeting Events

Individual clones were expanded into 24 well tissue culture plates, and genomic DNA prepared and analyzed by restriction digestion and Southern hybridization. One colony exhibited the pattern predicted for cells that have undergone homologous recombination and targeted gene replacement, and this culture was expanded for further characterization and use as a reporter cell line for CYP7 gene expression.

Figure 1:
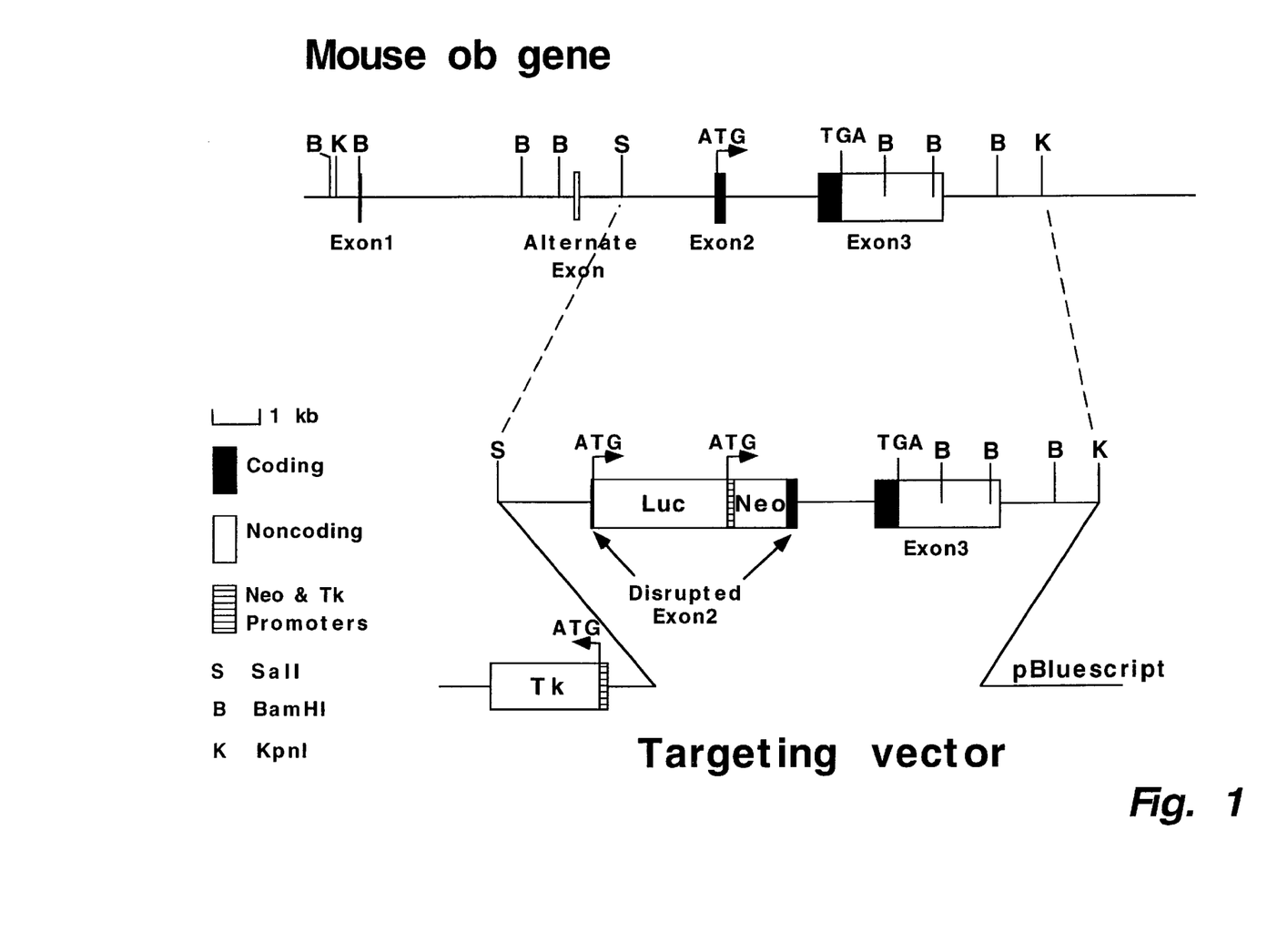
FIG. 1 shows the structures of the mouse ob gene and an exemplary "knock in" targeting vector.

2. Targeted Gene Replacement of Mouse ob (leptin) Gene a. Transgenic Primary Adipocytes Approximately 20 ug of a pBluescript gene-targeting construct containing about 2 kb of 5' flanking sequence and about 7 kb of 3' flanking sequence of the second exon of the ob gene was electroporated into D3 ES cells using a Bio-Rad gene pulser set at 25 uF/350 V. The construct effects the replacement of the second exon with a cassette containing the luciferase reporter and the neomycin resistance genes (FIG. 1). The construct also contained a thymidine kinase negative selection marker outside the cassette. After 9 days selection in 180 ug/ml G418 and 2 uM gancyclovir, drug-resistant clones were placed into 24-well plates and expanded in culture. Screening for correctly targeted clones was done by Southern analysis and suitable clones were injected into 3.5 day postcoital BALB/c blastocysts to generate chimeras. Heterozygote germline transmissions are identified by Southern analysis and bred as a stable strain. These are also intercrossed to yield homozygotes for the ob mutation.

To isolate primary adipocytes for screening assays, epididymal fat tissue is excised from two month old mice and prepared for cell culture by collagenase digestion as described in Rolland et al. (1995) J Biol Chem 270, 1102–2206. After digestion, primary adipocytes are isolated by filtration through 180 um sieves, also as described by Rolland et al. (supra).

b. Transgenic Cultured Adipocyte Cell Lines

The pBluescript gene-targeting construct described above and shown in FIG. 1 is electroporated into 3T3-F442A cells using a Bio-Rad gene pulser set at 25 uF/350 V. After approximately 14 days of positive/negative selection in 180 ug/ml G418 and 2 uM gancyclovir, drug-resistant clones were placed into 6-well plates and expanded in culture. Screening for correctly targeted clones was done by Southern analysis.

To obtain differentiated cells for screening assays, grow initial cultures of 50% confluent cells to 100% confluence, then continue incubation 10–14 days to obtain maximal differentiation.

Figure 2:
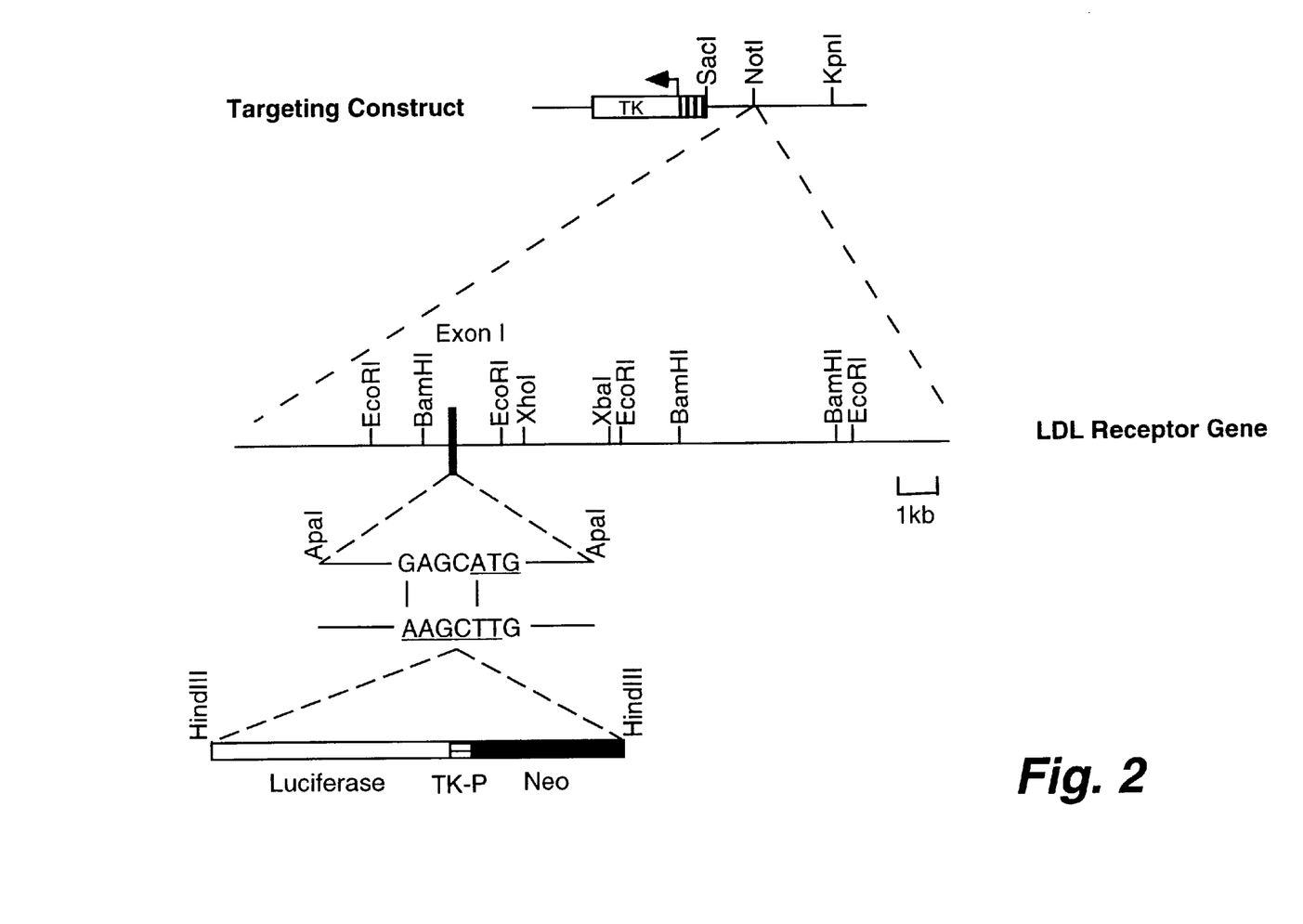
FIG. 2 shows the structure of a human LDLR-luciferase knock-in construct and the LDLR gene structure showing the vector insertion site.

3. Targeted Gene Replacement of Human LDL Receptor Gene a. Targeting Construct: Isolation of the Human LDLR Genomic Clone A genomic library was constructed in the GEM11 vector using HepG2 DNA that had been partially digested with Sau3A restriction endonuclease. Recombinant phage containing the LDLR gene were identified by hybridization to a radiolabeled LDLR cDNA probe. A 13.5 kilobasepair fragment containing sequences from approximately −4 kb to +9.5 kb (relative to transcriptional initiation) was isolated for preparation of the targeting construct. See FIG. 2.

b. Targeting Construct: Preparation of the LDLR:luciferase Targeting Construct

The 13.5 kb fragment of the LDLR gene was modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the Tn5 neomycin resistance gene under the transcriptional control of the HSV thymidine kinase promoter. This luciferase-neo cassette was inserted at the altered ATG site in exon 1 of the LDLR gene, positioning the reporter gene under the transcriptional control of the LDLR promoter. The chimeric LDLR:luciferase:neo gene was subsequently cloned into the pBluescript-MC1-HSVTk plasmid to allow dual selection with G418 and gancyclovir.

c. Isolation of LDLR "knock-in" Cell Lines: Transfection and Selection of Stably-Transformed Cell Lines The LDLR targeting construct was introduced into HepG2 cells by electroporation. Following recovery, the cells were maintained in media supplemented 1 mg/ml G418 and 2 uM gancyclovir for 3–4 weeks until individual colonies were observed. These G418R-GancR cells were isolated and propagated as individual cultures for further characterization.

d. Isolation of LDLR "knock-in" Cell Lines: Identification of Gene Targeting Events Individual clones were expanded into 24 well tissue culture plates, and genomic DNA was prepared and analyzed by restriction digestion and Southern hybridization. One clone exhibited the pattern predicted for cells that have undergone homologous recombination. The Southern analysis also indicated that one of the two allele of LDLR gene has been replaced by the luciferase-neo cassette. This clone was expanded for further characterization and use as a reporter cell line for LDLR gene expression.

e. Characterization of the "Knock-in Cell Line

To determine whether the expression of luciferase gene is regulated as the same way as the endogenous LDLR gene, RNA was prepared and analyzed by Northern hybridization. The results indicated that the luciferase mRNA was elevated when cells were cultured in lipid-depleted media and was suppressed in the presence of 25-hydroxycholesterol. The cholesterol-dependent regulation is the hallmark of LDLR gene expression. As indicated, the LDLR mRNA was regulated by in the presence or absence of cholesterol, albeit in this case the LDLR mRNA level was reduced to half due to the loss of one allele, which was replaced by the luciferase gene. The use of the luciferase knock-in cell line for LDLR gene expression was further validated by the luciferase activity, which was also regulated by cholesterol as predicted.

4. Targeted Gene Replacement of Human TNFα Gene a. Isolation of the Human TNFα Genomic Clone A genomic library is constructed in the λGEM11 vector using Thp1 DNA partially digested with Sau3A restriction endonuclease. Recombinant phage containing the TNFα gene are identified by hybridization to a radiolabeled TNFα cDNA probe and from these clones, a fragment encompassing the transcriptional and translational initiation sites isolated for additional characterization and modification.

b. Preparation of the TNFα:luciferase Targeting Construct

The fragment of the TNFα gene is modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette is inserted in exon 1 of the TNFα gene, positioning the reporter gene under the transcriptional control of the TNFα promoter. The chimeric TNFa:luciferase:neo gene was subsequently cloned into the pBluescript-MC1-HSVTk plasmid to allow dual selection with G418 and gancyclovir.

c. Isolation of TNFα "Knock-in" Cell Lines: Transfection and Selection of Stably-transformed Cell Lines The TNFα targeting construct is introduced into Thp1 cells by electroporation. Following recovery, the cells are maintained in media supplemented 1 mg/ml G418 and 2 $\mu$M gancyclovir for 3–4 weeks until isolated colonies are observed. These G418$^R$-Ganc$^R$ cells are isolated and propagated as individual cultures for further characterization.

d. Identification of Gene Targeting Events

Individual clones are expanded into 24 well tissue culture plates, and genomic DNA prepared and analyzed by restriction digestion and Southern hybridization. Colonies exhibiting the pattern predicted for cells that have undergone homologous recombination and targeted gene replacement are expanded for further characterization and use as reporter cell lines for TNFα gene expression.

5. Targeted Gene Replacement of Human E-selectin Gene a. Isolation of the Human E-selectin Genomic Clone A genomic library is constructed in the λGEM11 vector using ECV304 endothelial cell line DNA partially digested with Sau3A restriction endonuclease. Recombinant phage containing the E-selectin gene are identified by hybridization to a radiolabeled E-selectin cDNA probe and from these clones, a fragment encompassing the transcriptional and translational initiation sites isolated for additional characterization and modification.

b. Preparation of the E-selectin:luciferase Targeting Construct

The fragment of the E-selectin gene is modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette is inserted in exon 1 of the E-selectin gene, positioning the reporter gene under the transcriptional control of the E-selectin promoter. The chimeric E-selectin:luciferase:neo gene was subsequently cloned into the pBluescript-MC1-HSVTk plasmid to allow dual selection with G418 and gancyclovir.

c. Isolation of E-selectin "Knock-in" Cell Lines: Transfection and Selection of Stably-Transformed Cell Lines The E-selectin targeting construct is introduced into ECV304 cells by electroporation. Following recovery, the cells are maintained in media supplemented 1 mg/ml G418 and 2 $\mu$M gancyclovir for 3–4 weeks until isolated colonies are observed. These G418$^R$-Ganc$^R$ cells are isolated and propagated as individual cultures for further characterization.

d. Identification of Gene Targeting Events

Individual clones are expanded into 24 well tissue culture plates, and genomic DNA prepared and analyzed by restriction digestion and Southern hybridization. Colonies exhibiting the pattern predicted for cells that have undergone homologous recombination and targeted gene replacement are expanded for further characterization and use as reporter cell lines for E-selectin gene expression.

6. Targeted Gene Replacement of Human UCP-2 Gene a. Isolation of the Human UCP-2 Genomic Clone A genomic library is constructed in the λGEM11 vector using RD (Rhabdomyosarcoma) cell line DNA partially digested with Sau3A restriction endonuclease. Recombinant phage containing the UCP-2 gene are identified by hybridization to a radiolabeled UCP-2 cDNA probe and from these clones, a fragment encompassing the transcriptional initiation site isolated for additional characterization and modification.

b. Preparation of the UCP-2:luciferase Targeting Construct

The fragment of the UCP-2 gene is modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette is inserted in exon 1 of the UCP-2 gene, positioning the reporter gene under the transcriptional control of the UCP-2 promoter. The chimeric UCP-2:luciferase:neo gene was subsequently cloned into the pBluescript-MC1-HSVTk plasmid to allow dual selection with G418 and gancyclovir.

c. Isolation of UCP-2 "Knock-in" Cell Lines: Transfection and Selection of Stably-transformed Cell Lines The UCP-2 targeting construct is introduced into RD cells by electroporation. Following recovery, the cells are maintained in media supplemented 1 mg/ml G418 and 2 μM gancyclovir for 3–4 weeks until isolated colonies are observed. These $G418^R$-$Ganc^R$ cells are isolated and propagated as individual cultures for further characterization.

d. Identification of Gene Targeting Events

Individual clones are expanded into 24 well tissue culture plates, and genomic DNA prepared and analyzed by restriction digestion and Southern hybridization. Colonies exhibiting the pattern predicted for cells that have undergone homologous recombination and targeted gene replacement are expanded for further characterization and use as reporter cell lines for UCP-2 gene expression.

7. Targeted Gene Replacement of Mouse UCP-2 Gene a. Transgenic Primary Cells

Approximately 20 ug of a pBluescript gene-targeting construct containing about 2 kb of 5' flanking sequence and about 5 kb of 3' flanking sequence of the first exon of the mouse UCP-2 gene is electroporated into D3 ES cells using a Bio-Rad gene pulser set at 25 uF/350 V. The construct effects the replacement of the first exon with a cassette containing the luciferase reporter and the neomycin resistance genes. The construct also contains a thymidine kinase negative selection marker outside the cassette. After 9 days selection in 180 ug/ml G418 and 2 uM gancyclovir, drug-resistant clones are placed into 24-well plates and expanded in culture. Screening for correctly targeted clones is done by Southern analysis and suitable clones injected into 3.5 day postcoital BALB/c blastocysts to generate chimeras. Heterozygote germline transmissions are identified by Southern analysis and bred as a stable strain. These are also intercrossed to yield homozygotes for the UCP-2 mutation.

Primary muscle and/or adipoctyes are used. For example, to isolate primary adipocytes for screening assays, epididymal fat tissue is excised from two month old mice and prepared for cell culture by collagenase digestion as described in Rolland et al. (1995) J Biol Chem 270, 1102–2206. After digestion, primary adipocytes are isolated by filtration through 180 um sieves.

b. Transgenic Cultured Adipocyte Cell Lines

The pBluescript gene-targeting construct described above is electroporated into 3T3-F442A cells using a Bio-Rad gene pulser set at 25 uF/350 V. After approximately 14 days of positive/negative selection in 180 ug/ml G418 and 2 uM gancyclovir, drug-resistant clones were placed into 6-well plates and expanded in culture. Screening for correctly targeted clones was done by Southern analysis.

To obtain differentiated cells for screening assays, grow initial cultures of 50% confluent cells to 100% confluence, then continue incubation 10–14 days to obtain maximal differentiation.

8. Targeted Gene Replacement of Mouse Ob Receptor Gene a. Transgenic Primary Cells Approximately 20 ug of a pBluescript gene-targeting construct containing about 2 kb of 5' flanking sequence and about 5 kb of 3' flanking sequence of the first exon of the Ob receptor gene is electroporated into D3 ES cells using a Bio-Rad gene pulser set at 25 uF/350 V. The construct effects the replacement of the first exon with a cassette containing the luciferase reporter and the neomycin resistance genes. The construct also contains a thymidine kinase negative selection marker outside the cassette. After 9 days selection in 180 ug/ml G418 and 2 uM gancyclovir, drug-resistant clones are placed into 24-well plates and expanded in culture. Screening for correctly targeted clones is done by Southern analysis and suitable clones injected into 3.5 day postcoital BALB/c blastocysts to generate chimeras. Heterozygote germline transmissions are identified by Southern analysis and bred as a stable strain. These are also intercrossed to yield homozygotes for the Ob receptor gene mutation. Several primary cell types may be used. For example, to isolate primary thypothalamic neurons for screening assays, hypothalamic tissue is excised from two month old mice and prepared for cell culture by collagenase digestion and primary thypothalamic neurons are isolated.

b. Transgenic Cultured GTI Hypothalamic Neuronal Cell Lines

The pBluescript gene-targeting construct described above is electroporated into GTI cells using a Bio-Rad gene pulser set at 25 uF/350 V. After approximately 14 days of positive/negative selection in 180 ug/ml G418 and 2 uM gancyclovir, drug-resistant clones were placed into 6-well plates and expanded in culture. Screening for correctly targeted clones was done by Southern analysis. To obtain differentiated cells for screening assays, grow initial cultures of 50% confluent cells to 100% confluence, then continue incubation 10–14 days to obtain maximal differentiation.

9. Targeted Gene Replacement of Human ε (epsilon) Gene a. Isolation of the Human ε Genomic Clone A genomic library is constructed in the λGEM11 vector using BJAB cell line DNA partially digested with Sau3A restriction endonuclease. Recombinant phage containing the ε gene are identified by hybridization to a radiolabeled ε cDNA probe and from these clones, a fragment encompassing the transcriptional initiation site isolated for additional characterization and modification.

b. Preparation of the ε:luciferase Targeting Construct

The fragment of the ε gene is modified by site-directed mutagenesis in order to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette is inserted in the ε gene, positioning the reporter gene under the transcriptional control of the ε promoter. The chimeric ε:luciferase:neo gene was subsequently cloned into the pBluescript-MC1-HSVTk plasmid to allow dual selection with G418 and gancyclovir.

c. Isolation of ε "Knock-in" Cell Lines: Transfection and Selection of Stably-Transformed Cell Lines The ε targeting construct is introduced into BJAB cells by electroporation. Following recovery, the cells are maintained in media supplemented 1 mg/ml G418 and 2 μM gancyclovir for 3–4 weeks until isolated colonies are observed. These $G418^R$-$Ganc^R$ cells are isolated and propagated as individual cultures for further characterization.

d. Identification of Gene Targeting Events

Individual clones are expanded into 24 well tissue culture plates, and genomic DNA prepared and analyzed by restriction digestion and Southern hybridization. Colonies exhibiting the pattern predicted for cells that have undergone homologous recombination and targeted gene replacement are expanded for further characterization and use as reporter cell lines for ε gene expression.

10. Targeted Gene Replacement of Mouse STAT6 Gene a. Transgenic Primary Cells

Approximately 20 ug of a pBluescript gene-targeting construct containing about 5 kb of 5' flanking sequence and about 5 kb of 3' flanking sequence of the first exon of the STAT6 gene is electroporated into D3 ES cells using a Bio-Rad gene pulser set at 25 uF/350 V. The construct effects the replacement of the first exon with a cassette containing the luciferase reporter and the neomycin resistance genes. The construct also contains a thymidine kinase negative selection marker outside the cassette. After 9 days selection in 180 ug/ml G418 and 2 uM gancyclovir, drug-resistant clones are placed into 24-well plates and expanded in culture. Screening for correctly targeted clones is done by Southern analysis and suitable clones injected into 3.5 day postcoital BALB/c blastocysts to generate chimeras. Heterozygote germline transmissions are identified by Southern analysis and bred as a stable strain. These are also intercrossed to yield homozygotes for the STAT6 gene mutation. Several primary cell types may be used for screening assays, e.g. primary B-lymphocytes isolated from peripheral blood.

11. Targeted Gene Replacement of Human EPAS-1 Gene a. Isolation of the Human EPAS-1 Genomic Clone A genomic library is constructed in the λGEM11 vector using ECV304 endothelial cell line DNA partially digested with Sau3A restriction endonuclease. Recombinant phage containing the EPAS-1 gene are identified by hybridization to a radiolabeled EPAS-1 cDNA probe and from these clones, a fragment encompassing the transcriptional initiation site isolated for additional characterization and modification.

b. Preparation of the EPAS-1:luciferase Targeting Construct

The fragment of the EPAS-1 gene is modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette is inserted in exon 1 of the EPAS-1 gene, positioning the reporter gene under the transcriptional control of the EPAS-1 promoter. The chimeric EPAS-1:luciferase:neo gene was subsequently cloned into the pBluescript-MC1-HSVTk plasmid to allow dual selection with G418 and gancyclovir.

c. Isolation of EPAS-1 "Knock-in" Cell Lines: Transfection and Selection of Stably-transformed Cell Lines The EPAS-1 targeting construct is introduced into ECV304 cells by electroporation. Following recovery, the cells are maintained in media supplemented 1 mg/ml G418 and 2 μM gancyclovir for 3–4 weeks until isolated colonies are observed. These $G418^R$-$Ganc^R$ cells are isolated and propagated as individual cultures for further characterization.

d. Identification of Gene Targeting Events

Individual clones are expanded into 24 well tissue culture plates, and genomic DNA prepared and analyzed by restriction digestion and Southern hybridization. Colonies exhibiting the pattern predicted for cells that have undergone homologous recombination and targeted gene replacement are expanded for further characterization and use as reporter cell lines for EPAS-1 gene expression.

12. Targeted Gene Replacement of Human Utrophin Gene a. Isolation of the Human Utrophin Genomic Clone A genomic library is constructed in the λGEM11 vector using RD (Rhabdomyosarcoma) cell line DNA partially digested with Sau3A restriction endonuclease. Recombinant phage containing the utrophin gene are identified by hybridization to a radiolabeled utrophin cDNA probe and from these clones, a fragment encompassing the transcriptional and translational initiation sites isolated for additional characterization and modification. See, e.g. Tinsley et al. (1996) Nature 384, 349–353.

b. Preparation of the Utrophin:luciferase Targeting Construct

The fragment of the utrophin gene is modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette is inserted in exon 1 of the utrophin gene, positioning the reporter gene under the transcriptional control of the utrophin promoter. The chimeric utrophin:luciferase:neo gene was subsequently cloned into the pBluescript-MC1-HSVTk plasmid to allow dual selection with G418 and gancyclovir.

c. Isolation of Utrophin "Knock-in" Cell Lines: Transfection and Selection of Stably-Transformed Cell Lines The utrophin targeting construct is introduced into RD cells by electroporation. Following recovery, the cells are maintained in media supplemented 1 mg/ml G418 and 2 μM gancyclovir for 3–4 weeks until isolated colonies are observed. These $G418^R$-$Ganc^R$ cells are isolated and propagated as individual cultures for further characterization.

d. Identification of Gene Targeting Events

Individual clones are expanded into 24 well tissue culture plates, and genomic DNA prepared and analyzed by restriction digestion and Southern hybridization. Colonies exhibiting the pattern predicted for cells that have undergone homologous recombination and targeted gene replacement are expanded for further characterization and use as reporter cell lines for utrophin gene expression.

13. Targeted Gene Replacement of African Green Monkey HNF-1α Gene.

a. Isolation of the African Green Monkey HNF-1α Genomic Clone

A genomic library is constructed in the λGEM11 vector using CV-1 cell line DNA partially digested with Sau3A restriction endonuclease. Recombinant phage containing the African green monkey HNF-1α gene are identified by hybridization to a radiolabeled monkey HNF-1α cDNA probe and from these clones, a fragment encompassing the transcriptional and translational initiation site isolated for additional characterization and modification.

b. Preparation of the HNF-1α:luciferase Targeting Construct

The fragment of the HNF-1α gene is modified by site-directed mutagenesis in order to eliminate the authentic ATG codon used for translational initiation and to introduce restriction sites at this position for the insertion of the luciferase reporter gene. The final targeting construct incorporates the coding sequences for firefly luciferase fused to the polyadenylation signal from the SV40 early gene, as well as the G418 resistance cartridge containing the Tn5 neomycin resistance gene under the transcriptional control of the HSV thymidine kinase promoter. This luciferase-neo cassette is inserted in exon 1 of the HNF-1α gene, positioning the reporter gene under the transcriptional control of the HNF-1α promoter. The chimeric HNF-1α:luciferase:neo gene was subsequently cloned into the pBluescript-MC1-HSVTk plasmid to allow dual selection with G418 and gancyclovir.

c. Isolation of HNF-1α "Knock-in" Cell Lines: Transfection and Selection of Stably-transformed Cell Lines The HNF-1α targeting construct is introduced into CV-1 cells by electroporation. Following recovery, the cells are maintained in media supplemented 1 mg/ml G418 and 2 $\mu$M gancyclovir for 3–4 weeks until isolated colonies are observed. These $G418^R$-$Ganc^R$ cells are isolated and propagated as individual cultures for further characterization.

d. Identification of Gene Targeting Events

Individual clones are expanded into 24 well tissue culture plates, and genomic DNA prepared and analyzed by restriction digestion and Southern hybridization. Colonies exhibiting the pattern predicted for cells that have undergone homologous recombination and targeted gene replacement are expanded for further characterization and use as reporter cell lines for HNF-1α gene expression.

14. Cell-based Transcription Assay.

Aliquot 100 ul cell suspension ($10^4$–$10^5$ primary or cultured, differentiated cells) into each well of 96-well plate under sterile conditions Add compound or extract to 10 uM final concentration Incubate 6–18 hrs at 37° C.

Remove incubation media

Add 100 ul lysis/luciferin buffer containing 1.0% non-ionic detergent (Triton x-100), 530 uM ATP, 270 uM coA and 470 uM luciferin (Promega).

Measure luciferase-derived luminescence on automated Torcon AML-34 and 7710 Microplate Luminometer (Cambridge Technologies, Inc.) luminometers.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated genetic knock-in cell, wherein said cell is, or is a progeny of, a genetic knock-in primary cell obtained from a transgenic mouse made by homologous recombination of a targeted native allele with a transgene comprising a sequence encoding a reporter flanked by flanking sequences which effect the homologous recombination of said transgene with said native allele, wherein the expression of said reporter is under the control of native gene expression regulatory sequences of said native allele.

2. The genetic knock-in cell of claim 1, wherein said knock-in cell results from the replacement of a portion of said native allele with a sequence encoding said reporter.

3. The genetic knock-in cell of claim 1, wherein said reporter is luciferase.

4. A cell-based method for screening for modulators of a targeted gene expression, said method comprising steps:

(a) isolating a genetic knock-in primary cell from a transgenic mouse made by homologous recombination of a targeted native allele with a transgene comprising a sequence encoding a reporter flanked by flanking sequences which effect the homologous recombination of said transgene with said native allele, wherein the expression of said reporter is under the control of native gene expression regulatory sequences of said native allele, (b) determining a first reporter expression level in a first isolated cell wherein said first isolated cell is, or is a progeny of said genetic knock-in cell;

(c) contacting a second isolated cell wherein said second isolated cell is, or is a progeny of said genetic knock-in cell with a candidate agent under conditions whereby but for the presence of said agent, said reporter is expressed at said first reporter expression level;

(d) determining a second reporter expression level in said second isolated cell;

(e) comparing said first expression level with said second expression level, wherein a difference between said first and second expression levels indicates that said candidate agent modulates the targeted gene expression.

5. The method of claim 4, wherein said second isolated cell is in a suspension of identical cells, said reporter is luciferase, said contacting step comprises depositing aliquots of said suspension into wells of a plate under sterile conditions, adding said agent to said aliquots and incubating said aliquots 6–18 hours, and said measuring step comprises adding a lysing detergent, ATP, coenzyme A and luciferin to said aliquots and measuring luciferase-derived luminescence.

6. The genetic knock-in cell of claim 1, wherein said knock-in cell is a blood borne cell.

7. The genetic knock-in cell of claim 1, wherein said knock-in cell is a lymphocyte or macrophage.

8. The genetic knock-in primary cell of claim 1, wherein said knock-in cell is a structurally associated cell.

9. The genetic knock-in primary cell of claim 1, wherein said knock-in cell is a hepatocyte, muscle cell or neuron.

10. The method of claim 4, wherein said genetic knock-in cell is a blood borne cell.

11. The method of claim 4, wherein said genetic knock-in cell is a lymphocyte or macrophage.

12. The method of claim 4, wherein said genetic knock-in cell is a structurally associated cell.

13. The method of claim 4, wherein said genetic knock-in cell is a hepatocyte, muscle cell or neuron.

* * * * *